United States Patent
Grudo et al.

(10) Patent No.: US 9,408,523 B2
(45) Date of Patent: Aug. 9, 2016

(54) DISPOSABLE AIR/WATER VALVE FOR AN ENDOSCOPE

(75) Inventors: Dina Grudo, Allen, TX (US); Christopher Steven Adams, Montgomery, TX (US); Don Byrne, Montgomery, TX (US)

(73) Assignee: MEDIVATORS INC., Minneapolis, MN (US)

( * ) Notice: Subject to any disclaimer, the term of this patent is extended or adjusted under 35 U.S.C. 154(b) by 219 days.

(21) Appl. No.: 13/989,649

(22) PCT Filed: Nov. 30, 2011

(86) PCT No.: PCT/US2011/062628
§ 371 (c)(1),
(2), (4) Date: Jul. 17, 2013

(87) PCT Pub. No.: WO2012/075131
PCT Pub. Date: Jun. 7, 2012

(65) Prior Publication Data
US 2013/0303844 A1    Nov. 14, 2013

Related U.S. Application Data (60) Provisional application No. 61/418,191, filed on Nov. 30, 2010.

(51) Int. Cl.
*A61B 1/12* (2006.01)
*A61B 1/00* (2006.01)
*A61B 1/015* (2006.01)

(52) U.S. Cl.
CPC ......... *A61B 1/00064* (2013.01); *A61B 1/00068* (2013.01); *A61B 1/015* (2013.01); *Y10T 29/49417* (2015.01)

(58) Field of Classification Search
USPC .................................................. 600/156–159
See application file for complete search history.

(56) References Cited

U.S. PATENT DOCUMENTS 3,958,566 A * 5/1976 Furihata ............. A61B 1/00068
                                                                    137/605
4,261,343 A    4/1981 Ouchi et al.
(Continued)

FOREIGN PATENT DOCUMENTS

EP    0055394    3/1985

OTHER PUBLICATIONS

International Search Report and Written Opinion by the International Searching Authority Filed in Application No. PCT/US2011/06262B on Nov. 30, 2011 and mailed on Mar. 27, 2012.
(Continued)

*Primary Examiner* — Matthew J Kasztejna
(74) *Attorney, Agent, or Firm* — Sorell, Lenna & Schmidt LLP; William D. Schmidt, Esq.

(57) ABSTRACT

A disposable air/water valve may include a main stem providing an air passage through the center bore of the main stem. A method for manufacturing a disposable air/water valve may include several steps. The main stem is molded, and placed in a mold for over-molding seals onto the main stem. Prior to the next steps, the retaining ring, button cap, and boot may be molded. The back end of the main step is placed through the center of the retaining ring and resilient member (e.g. spring). The button cap is then placed on and secured to the main stem.

23 Claims, 9 Drawing Sheets

(56) References Cited

U.S. PATENT DOCUMENTS

| | | | |
|---|---|---|---|
| 4,361,138 A | 11/1982 | Kinoshita | |
| 4,412,531 A * | 11/1983 | Chikashige | A61B 1/00068 600/104 |
| 5,391,145 A | 2/1995 | Dorsey, III | |
| 5,522,796 A | 6/1996 | Dorsey, III | |
| 5,871,441 A * | 2/1999 | Ishiguro | A61B 1/122 600/133 |
| 6,346,075 B1 | 2/2002 | Arai et al. | |
| 6,908,429 B2 * | 6/2005 | Heimberger | A61B 1/00068 600/159 |
| 2004/0238014 A1 | 12/2004 | Halstead et al. | |

OTHER PUBLICATIONS

Olympus Medical Systems Corp., "Olympus® Evis Exera GIF/CF/PCF Type 160 Series Operation Manual", pp. 1-102, published 2003.

Olympus America, Inc., "Endoscope Channel Guide", p. 1 of 1, published 2003.

\* cited by examiner

DISPOSABLE AIR/WATER VALVE FOR AN ENDOSCOPE

This application claims the benefit of the filing date of U.S. Provisional Patent Application Ser. No. 61/418,191, filed on Nov. 30, 2010. This entire disclosure is hereby incorporated by reference into the present disclosure.

FIELD

This application relates to medical instrument systems. More particularly, air and water valves for endoscopes and methods for manufacturing such valves.

BACKGROUND

Endoscopes are well-known in the art and are commonly used for numerous medical procedures. A control section of an endoscope may include a suction cylinder, air/water cylinder, and the like. Valves may be inserted into these cylinders to control various functions of the endoscope.

For example, an air/water valve for an endoscope may be inserted into an air/water cylinder of the endoscope to provide air and water to the endoscope. When the air/water valve is in a normal position, air escapes from a vent in the valve. When insufflation is desired, an operator places a finger over the vent, which redirects the air towards the distal end of the endoscope. When the operator engages the air/water valve (e.g. by depressing the valve), air is redirected to a water bottle and creates pressure in the bottle that causes water to flow towards the distal end of the endo scope.

After each use, an endoscope will undergo cleaning, disinfection, sterilization, and the like to prevent the spread of disease, germs, bacteria, illness, and the like. Many components of an endoscope may be reusable, such as an air/water valve, and must also be cleaned, disinfected, and/or sterilized between uses. Unfortunately, there is usually a great expense associated with maintaining sterility of the equipment.

Reusable air/water valves may be assembled from the combination of several metal, plastic, and/or rubber components. As such, there are significant costs associated with the manufacturing of reusable air/water valves.

Thus, there is a need to develop new disposable air/water valves and methods that reduce or eliminate the need for repeated cleaning, disinfection, and sterilization and reduce or eliminate the risk of infecting the patient. Air/water valves that have reduced risk of clogging would also be very useful.

SUMMARY

New devices and methods are provided that reduce or eliminate the risk of contaminating the endoscope and reduce or eliminate the risk of infecting the patient. The air/water valve provided is lightweight, easy to use and, in some embodiments, improves conducting air and/or water to the endoscope.

Various embodiments of a disposable air/water valve for an endoscope are discussed herein, including manufacturing processes for disposable air/water valves.

In some embodiments, a disposable air/water valve is provided and may include a main stem providing a passage through the center bore of the main stem. The main stem is provided with four seals secured in retaining areas provided by the main stem. The disposable air/water valve also includes a button/cap that may be secured to the back end of the main stem, and a resilient member (e.g., spring, rubber, elastic, etc.) positioned between a retaining ring/boot and the button cap.

In some embodiments, a method is provided for manufacturing a disposable air/water valve and may include several steps. A main stem is precision molded, then placed in a mold for over-molding seals onto the main stem. Prior to the next steps, the retaining ring and button cap are molded. The boot is over-molded onto the retaining ring. The back end of the main stem is placed through the center of the retaining ring/boot and resilient member (e.g., spring, rubber, elastic, etc.). The button cap is then placed on and secured to the main stem.

In some embodiments, a method is provided for manufacturing a disposable air/water valve comprising: molding a main stem; placing the main stem in a first mold, wherein at least one seal is over-molded onto the main stem; molding a retaining ring; molding a button cap; placing a back end of the main stem through the center of the retaining ring and a resilient member (e.g., spring, rubber, elastic, etc.); and placing the button cap on the main stem and securing the button cap to the main stem.

In some embodiments, there is an air/water valve assembly comprising: a main stem having a proximal end, the main stem comprising a plurality of ridges and grooves disposed circumferentially about the main stem, the plurality of ridges and grooves being monolithic with the main stem and the main stem comprising a first opening disposed at the proximal end and running along a longitudinal axis of the main stem, and a second opening disposed transverse to the first opening, the first and second openings for allowing passage of air and/or fluid through at least a portion of the main stem.

In some embodiments, there is an air/water valve assembly comprising: a main stem having a proximal end, the main stem comprising a plurality of ridges and grooves disposed circumferentially about the main stem, the plurality of ridges and grooves being monolithic with the main stem and the main stem comprising a first opening disposed at the proximal end and running along a longitudinal axis of the main stem, and a second opening disposed transverse to the first opening, the first and second openings intersecting with each other and configured to allow passage of air and/or fluid through at least a portion of the main stem; a plurality of seals disposed in the plurality of grooves disposed circumferentially about the main stem; a retainer ring contacting and disposed around the main stem; a button head or cap contacting the proximal end of the main stem and a resilient member (e.g., spring, rubber, elastic, etc.) contacting the retainer ring and the button head, wherein application of a downward force to the button head causes the main stem to move in a downward position.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "a seal" includes one, two, three or more seals.

We refer now to the drawings wherein depicted elements are not necessarily shown to scale and wherein like or similar elements are designated by the same reference numeral through the several views.

Referring to the drawings in general, it will be understood that the illustrations are for the purpose of describing particular embodiments of the disclosure and are not intended to be limiting thereto.

While most of the terms used herein will be recognizable to those of ordinary skill in the art, it should be understood that when not explicitly defined, terms should be interpreted as adopting a meaning presently accepted by those of ordinary skill in the art.

Figure 1:
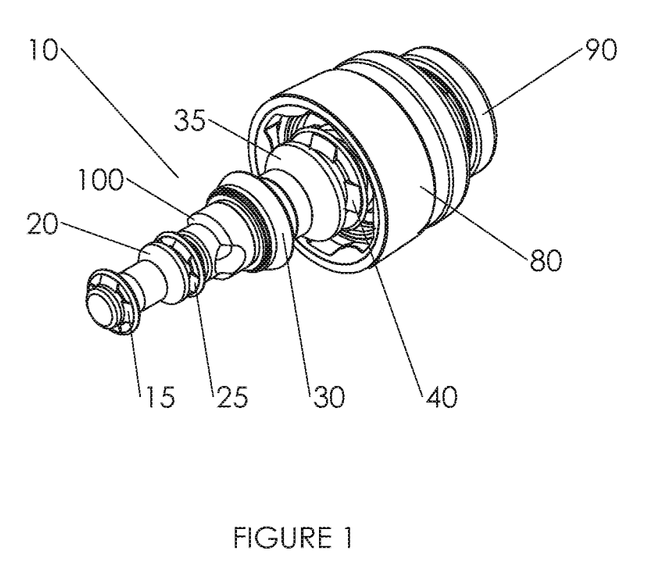
FIG. 1 illustrates an isometric view of an embodiment of a reusable air/water valve.
Figure 2:
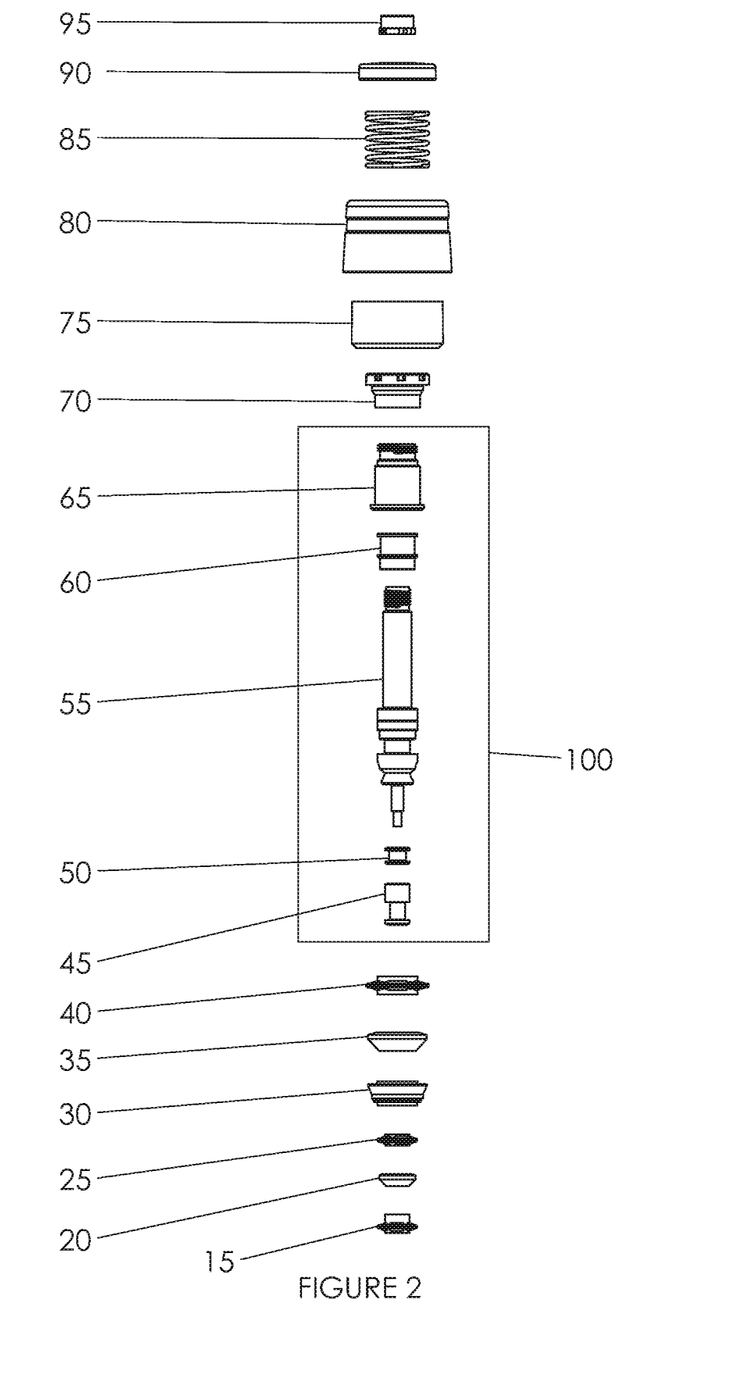
FIG. 2 illustrates an exploded view of an embodiment of a reusable air/water valve.

Referring FIG. 1 and FIG. 2, FIG. 1 is an isometric view of a reusable air/water valve 10, and FIG. 2 is an exploded view of the components of a reusable air/water valve 10. While the reusable air/water valve 10 shown is suitable for use with Olympus® endoscopes, other embodiments of reusable air/water valves may be suitable for use with other types of endoscopes, such as Pentax®, Fujinon®, or the like.

Reusable air/water valve 10 may provide a main stem 55 that receives several components 45, 50, 60, 65 and 70 that are formed from a suitable material combination of material(s), such as stainless steel or the like. Components 45, 50, 60, 65 and 70 may be secured to main stem 55 by threading, welding, staking or a suitable adhesive to form an assembly 100. However, these components 45, 50, 60, 65 and 70 are not monolithic with the main stem (e.g., they are not one piece) and therefore, this can complicate the manufacturing process.

Seals 15, 25, 30, 40 and aligners 20, 35 of the reusable air/water valve may be secured on assembly 100. Assembly 100 may be inserted through a resilient member (e.g., spring, rubber, elastic, etc.) 85 and a retaining ring 75. Next, component 70, a vent 95, a button head or cap 90 may be secured to assembly 100 using threading, welding, a suitable adhesive, or any other suitable method. Boot 80 may then be placed over retaining ring 75 and secured in place with an attachment means (e.g., adhesive, glue, molding, over molding, curing with UV light, welding or the like or combinations thereof) to complete the assembly of reusable air/water valve 10. Vent 95 may be color coded or color matched to indicate that valve is an air/water valve (e.g. blue, red for biohazard, etc.).

Seals 15, 25, 30, 40 and boot 80 are formed from a suitable material, such as rubber, plastic, silicone, or the like. Aligners 20, 35, retaining ring 75, button head 90, and vent 95 are formed from a suitable material, such as metal, plastic, silicon, stainless steel, or the like or combinations thereof.

However, retaining ring 75, button head 90, and vent 95 may be formed of a more rigid material than seals 15, 25, 30, and 40 because they are subjected to forces exerted by resilient member (e.g., spring, rubber, elastic, etc.) 85 and an operator. Aligners 20 and 35 may be formed from a material that will not create significant friction force as it slides within the air/water cylinder.

Figure 3:
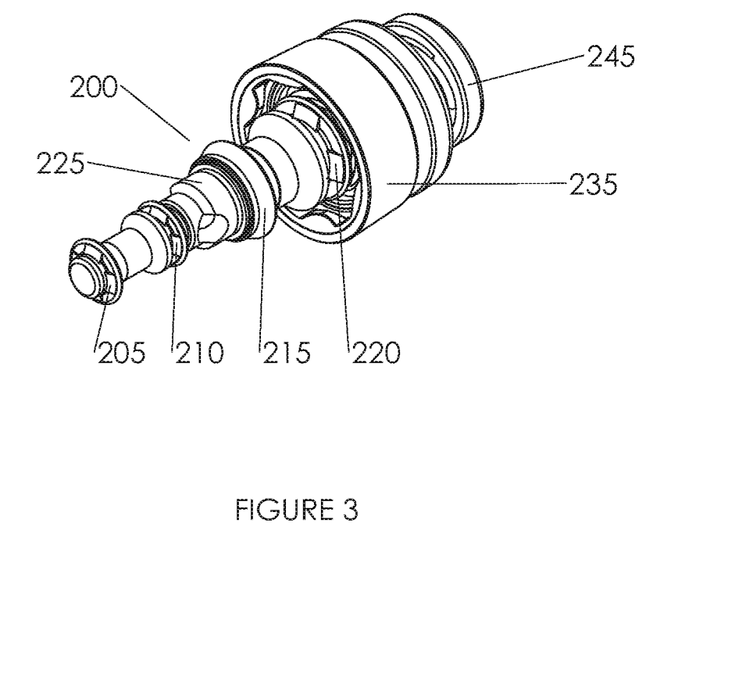
FIG. 3 illustrates an isometric view of an embodiment of a disposable air/water valve.
Figure 4:
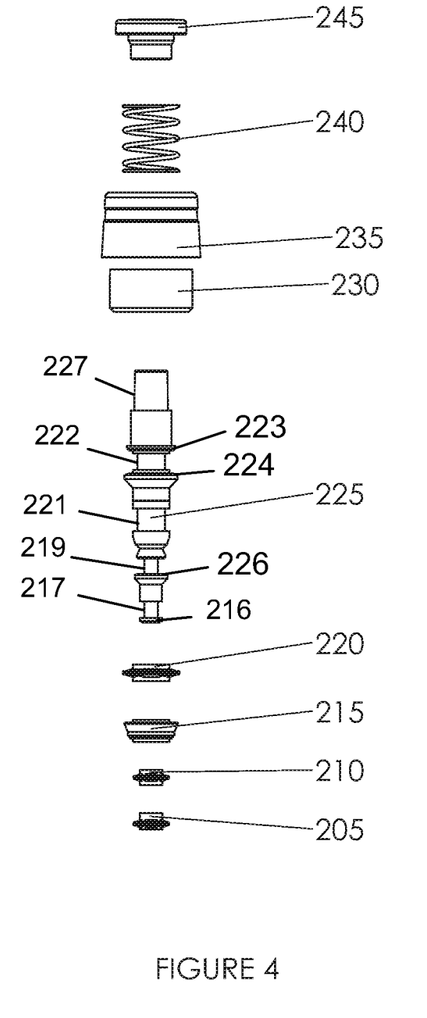
FIG. 4 illustrates an exploded view of an embodiment of a disposable air/water valve.

Referring to FIG. 3 and FIG. 4, FIG. 3 is an isometric view of an illustrative implementation of a disposable air/water valve 200, and FIG. 4 is an exploded view of an illustrative embodiment of a disposable air/water valve 200 of FIG. 3. Disposable air/water valve 200 is appreciably simplified, in comparison to a reusable water valve, into nine total components—seals 205, 210, 215, 220, main stem 225, retaining ring 230, boot 235, resilient member (e.g., spring, rubber, elastic, etc.) 240, and button cap 245. Main stem 225 is monolithic (e.g., a single piece) having grooves 227, 222, 221, 219, 217, and ridges 216, 223, 224 and 226 that are molded as part of the main stem. These ridges and/or grooves can be rigid or they can be flexible.

Unlike the non-disposable air/water valves that are not monolithic as many of the ridges and/or grooves are molded separately and contain different material than the main stem, which often comprise metal, the monolithic main stem (one piece) of the disposable air/water valve comprises a plurality of ridges and grooves that are the same material as the main stem. In some embodiments, the seals 205, 210, 215, or 220 can be set into the grooves of the main stem.

One or more components of the device of the current application (e.g., seals 205, 210, 215, 220, main stem 225, retaining ring 230, boot 235, resilient member (e.g., spring, rubber, elastic, etc.) 240, and button cap 245) can be made from a suitable material such as for example, polyurethane, polyurea, polyether(amide), PEBA, thermoplastic elastomeric olefin, copolyester, styrenic thermoplastic elastomer, carbon fiber, glass fiber, ceramics, methacrylates, poly (N-isopropylacrylamide), PEO-PPO-PEO (pluronics), rubber, plastic (e.g., polycarbonates), ABS, MABS, silicone, or the like or combinations thereof.

Figure 5:
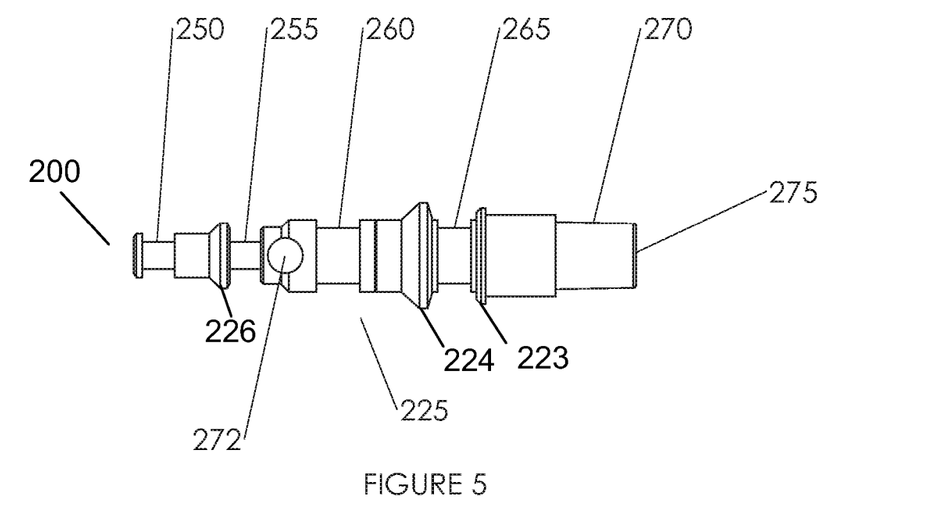
FIG. 5 illustrates an enlarged view of an embodiment of a main stem.

FIG. 5 is an enlarged view of an illustrative implementation of main stem 225. Main stem 225 is precision molded in one piece for accuracy and rigidity. Main stem 225 may be color coded to identify the product as an air/water valve. Color coding of main stem 225 allows the air/water valve to be easily identified and eliminates the need for a separately color coded component, such as vent 95 in FIG. 1. Further, the color coding also identifies disposable air/water valve as a disposable valve. Main stem 225 provides several seal retaining regions 250, 255, 260, 265 or grooves for keeping seals 205, 210, 215, 220 in desired positions on main stem 225. Ridges 223, 224 and 226, like the retaining regions or grooves, are molded as part of the main stem. Seals 205, 210, 215, 220 of FIG. 4 may be over-molded to main stem 225 or appropriately secured to the main stem. Over-molding the seals on the main stem avoids the need to slide the seals onto main stem 225, which could tear or damage the seals during assembly.

In reusable air/water valve 10 shown in FIGS. 1 and 2, assembly 100 is separated into several components to avoid sliding seals over component with a significantly larger diameter than the internal diameter of the seal, which could cause damage to the seal during assembly. Over-molding the seals onto main stem 225 avoids the need to separate the main stem into several components, which significantly reduces the number of components and assembly steps. Main stem 225 provides an opening 272 and a passage 275 passing through main stem 225. Opening 272 and passage 275 allow air to escape the disposable air/water valve 200. Additionally, an internal bore of main stem 225 is hollow from opening 272 to an end 270, which creates a passageway or vent 275 for air to escape air/water valve 200. When end 270 is not covered by an operator, air may travel into passage 275 and up the internal bore of main stem 225. Operation of an air/water valve in an endoscope is discussed in further detail below.

Figure 6:
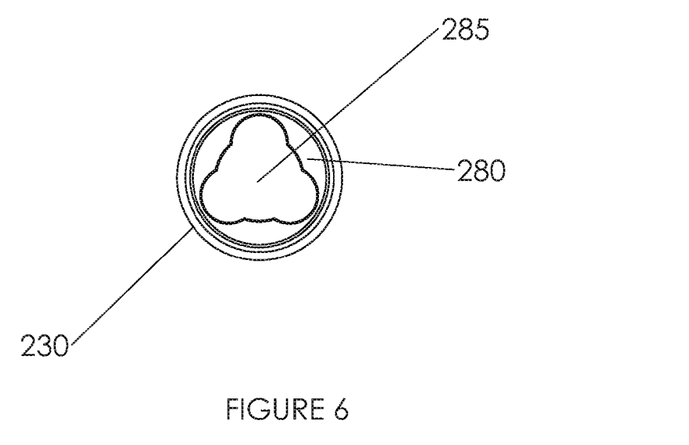
FIG. 6 illustrates is a top view of an embodiment of a retaining ring.

Retaining ring 230 (of FIG. 4) provides a diaphragm 280, as shown in FIG. 6, with an opening 285 for receiving end 270 of main stem 225. While opening 285 is shaped as a larger diameter circle with three semi-circular cutouts (one shown as 281) along the radius of the larger diameter circle, it should be recognized that any other suitably shaped opening 285 may be utilized (e.g. square, triangle etc.). End 270 of main stem 225 may be placed through retaining ring 230 and resilient member (e.g., spring, rubber, elastic, etc.) 240 and secured to button cap 245 (of FIG. 4).

The outer diameter of end 270 of main stem 225 is smaller than a hollow center bore of button cap 245, thereby allowing end 270 of main stem 225 to be inserted into the center bore of button cap 245. End 270 may protrude slightly from button cap 245 to provide an operator with tactile confirmation that the vent hole is sealed with the finger. Main stem 225 may be secured to button cap 245 using ultrasonic welding, a suitable adhesive, mechanical attachment (e.g. threading or the like) or any suitable attachment method.

In another implementation of the disposable air/water valve 200, main stem 225 and button cap 245 may be molded as a single piece.

Seals 205, 210, 215, 220 are molded on main stem 225. Then main stem 225 is inserted through the center of retaining ring 230. Above seal retaining region 265 (of FIG. 5), main stem 225 may be modified to provide grooves or the like in another implementation. Retaining ring 230 of FIG. 4 may be modified to provide a larger diameter opening 285 to allow the bottom of main stem 225 to pass through the opening. Further, retaining ring 230 of FIG. 4 may provide protrusions that fit into the grooves to secure retaining ring 230 to the combined main stem and button cap 245. Boot 235 may be over-molded around retaining ring 230.

In other implementations, boot 235 may be molded separately from retaining ring 230 and placed on the retaining ring 230 during assembly. Main stem 225 may be color coded or color matched by forming main stem 225 from a colored material, painting, or the like. The color coding of disposable air/water valve 200 is easily visible when the valve is out of an endoscope, thereby making air/water valve 200 easy to identify as an air/water valve and a disposable valve. Further, the color coding eliminates the need for a separate color components (e.g. vent 95 of FIG. 2) necessary to produce an air/water valve. Because main stem 225 is inserted into the center bore of button cap 245, the color coding of main stem 225 is also visible from the top of button cap 245 or when disposable air/water valve 200 is placed in the air/water cylinder of the endoscope.

The outside diameter of the top end of button cap 245 is larger than the diameter of resilient member (e.g., spring, rubber, elastic, etc.) 240, which resumes its original shape or position after being compressed, and the inside diameter of opening 285 in diaphragm 280 is smaller than the diameter of resilient member (e.g., spring, rubber, elastic, etc.) 240 to retain resilient member (e.g., spring, rubber, elastic, etc.) 240 between retaining ring 230 and button cap 245.

When button cap 245 is depressed by an operator, resilient member (e.g., spring, rubber, elastic, etc.) 240 is compressed causing button cap 245 to move towards retaining ring 230. Because main stem 225 is secured to button cap 245, it also moves when button cap 245 is depressed, thereby allowing the trumpet-like valve to move into alignment with a desired endoscope port. When the operator releases button cap 245, resilient member (e.g., spring, rubber, elastic, etc.) 240 forces button cap 245 away from retaining ring 230, which causes retaining ring 230 to move along main stem 225. However, the opening 285 in diaphragm 280 of retaining ring 230 is smaller than the diameter of main stem 225 just above seal retaining region 265, thereby preventing retaining ring 230 from advancing past seal retaining region 265 on main stem 225.

Seals 205, 210, 215, 220 are formed from pliable material suitable for creating a seal, such as rubber, polymeric material(s), or a suitable material or a combination of suitable material(s). Boot 235 may also be made from a pliable material for ease of assembly e.g., a material that allows boot 235 to be slid over retaining ring 230. Retaining ring 230, main stem 225, and button cap 245 are formed from a suitable material or combination of material(s), such as plastic, polymeric material(s), or the like. However, retaining ring 230, main stem 225, and button cap 245 can be formed of a more rigid material than seals 205, 210, 215, 220 and boot 235. It may be preferable to have a more rigid retaining ring 230, main stem 225, and button cap 245 because they are subjected to forces exerted by resilient member (e.g., spring, rubber, elastic, etc.) 240, an operator, or the like.

Figure 7A:
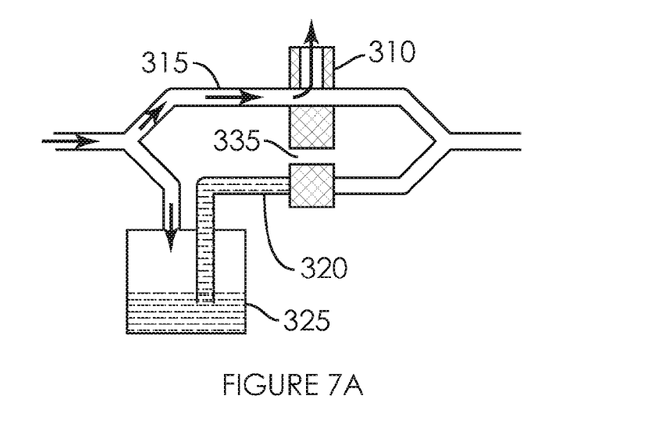
FIG. 7A-C illustrate the general operation of an air/water valve in an endoscope.
Figure 7B:
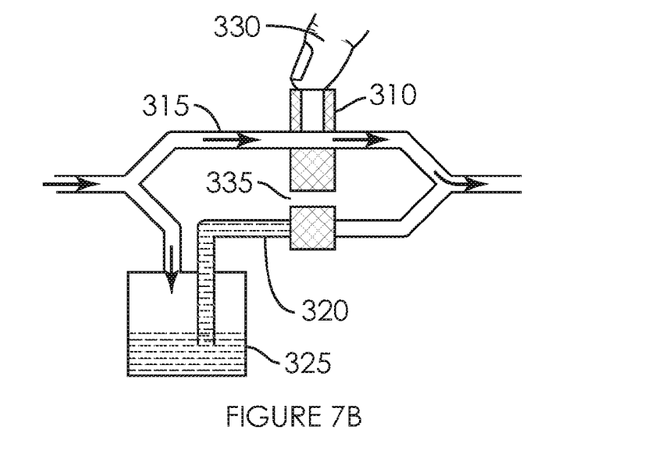
Figure 7C:
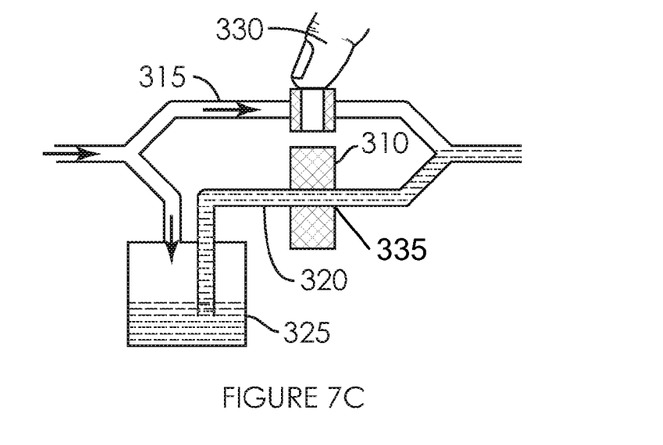

FIGS. 7A-C are illustrative implementations of the operation of an air/water valve in an endoscope. Note that the discussion in reference to FIGS. 7A-C are directed toward a generic air/water valve, which can include the reusable air/water valve 10 discussed in FIG. 1 or disposable air/water valve 200 discussed in FIG. 3. The discussion merely provides an explanation of how an air/water valve generally operates in an endoscope.

In FIG. 7A, air/water valve 310 is positioned in the air/water cylinder of an endoscope and is shown in an un-actuated position. The endoscope provides an air channel 315 for air and a water channel 320 for water. Air channel 315 and water channel 320 are connected to water bottle 325. Water channel 320 extends into the fluid contained in water bottle 325. When air/water valve 310 is placed in the air/water cylinder of the endoscope, air/water valve passes through air channel 315 and water channel 320. Air flow (provided by an air pump or the like), shown by the arrows, may flow into water bottle 325 and air channel 315. However, because water bottle 325 is sealed and water channel 320 is blocked by air/water valve 310, air tends to flow down air channel 315 towards air/water valve 310. In the un-actuated position with the air vent uncovered, air/water valve 310 allows air to escape from a vent. For example, with disposable air/water valve 200, air would flow into passage 275 through the internal bore of main stem 225 and out end 270 of the disposable air/water valve 200. Note that disposable air/water valve 200 in FIG. 3 provides several seals 205, 210, 215, 220 that prevent air or water from leaking from air channel 315 or water channel 320. Opening 335 of the air-water valve 310 is not aligned with the water channel and, there is no movement of water away from the water bottle, as the water channel is blocked.

In FIG. 7B, air/water valve 310 in the air/water cylinder of an endoscope is shown in an un-actuated position with the vent blocked by an operator's finger 330 or the like. Because water bottle 325 is sealed and water channel 320 is blocked by air/water valve 310, air tends to flow down air channel 315 towards air/water valve 310. However, when the air vent of air/water valve 310 is blocked by the operator 330, air flows past air/water valve 310 towards the distal end of an endoscope. This allows the operator to insufflate a body cavity by blocking the air vent of air/water valve 310 without actuating the valve. In FIG. 7B, opening 335 of the air/water valve 310 is shown blocked.

In FIG. 7C, air/water valve 310 is shown in an actuated position. When air/water valve 310 is actuated the resilient member (e.g., spring, rubber, elastic, etc.) in the valve is compressed and air channel 315 is blocked by the air/water valve 310. However, actuating air/water valve 310 moves opening 335 of the valve into water channel 310, thereby creating a passageway for fluid to pass through air/water valve 310. Because air channel 315 is blocked by operator 330 pressing down on the valve, air flows into water bottle 325. As the air pressure in water bottle 325 increases, fluid is forced from water bottle 325 into water channel 320. By actuating air/water valve 310, the operator causes water to flow towards the distal end of the endoscope for rinsing, irrigation, or the like.

Figure 8A:
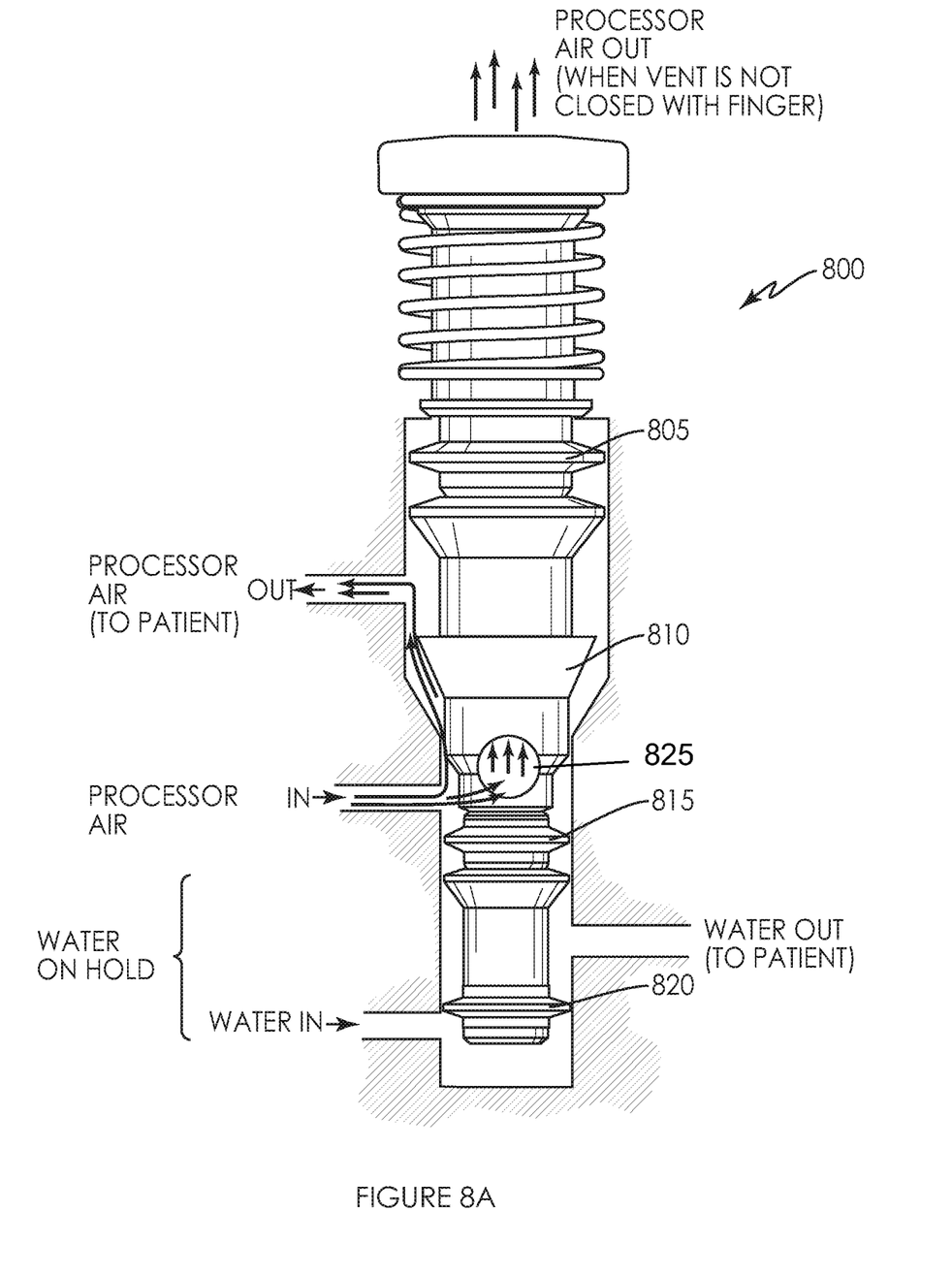
FIGS. 8A and 8B illustrate the general operation of a disposable air/water valve in an endoscope.
Figure 8B:
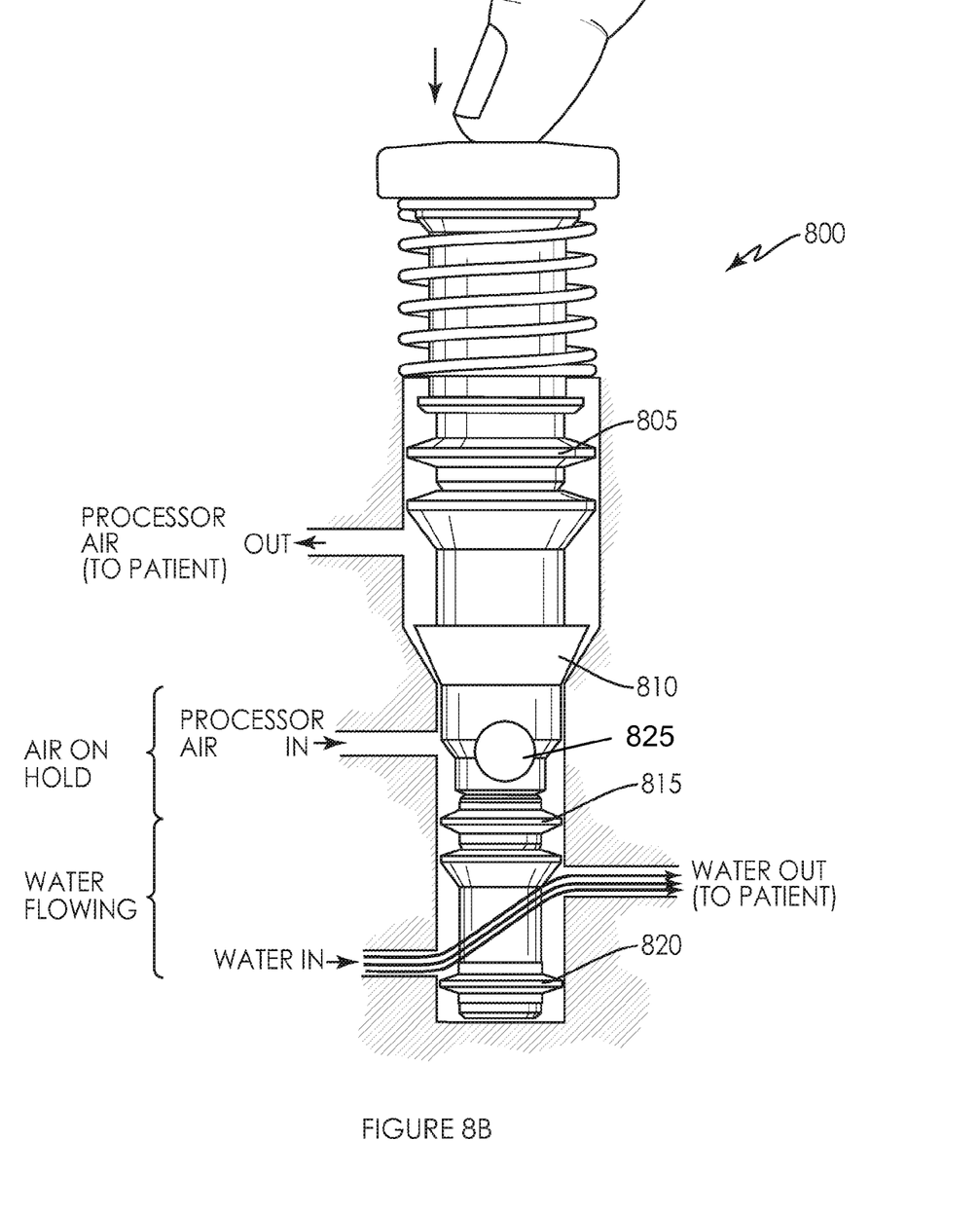

FIGS. 8A and 8B are illustrative implementations of the operation of a disposable air/water valve 800 in an endoscope. In FIG. 8A, disposable air/water valve 800 is shown in an undepressed or unactuated position. Seals 810 (see seals 30 and 215 in FIGS. 2 and 4) and 815 (see seals 25 and 210 in FIGS. 2 and 4) prevent air from escaping the chamber between seals 810 and 815. Opening 825 (see also opening 272 in FIG. 5) allows the air to escape through the central bore of disposable air/water valve 800 as shown. Note that air/water valve 800 is shown without a boot and retaining ring for illustrative purposes only. When an operator places a finger on top of disposable air/water valve 800 to prevent air from escaping, pressure in the chamber between seals 810 and 815 increases.

If the operator has created a sufficient seal by substantially blocking air flow out of the top of disposable air/water valve 800, the wall of seal 810 collapses to allow air to flow past the seal. Seal 805 (see also seals 40 and 220 in FIGS. 2 and 4) prevents air from escaping out through the air/water cylinder of the endoscope. As a result, the air can only escape out though the outlet to the patient.

Seal 820 (see also seals 15 and 205 in FIGS. 2 and 4) prevent water from escaping past disposable air/water valve 800 in the un-actuated position. Seal 820 separates the water inlet from the water outlet. It should be noted that residual water from previously depressing disposable air/water valve 800 may remain between seals 815 and 820. Seal 815 prevents the residual water from escaping further up the air/water cylinder of endoscope.

In FIG. 8B, disposable air/water valve 800 is depressed in the air/water cylinder of an endoscope. Seals 805 and 810 prevent air from the air output (i.e. air from the patient) from back flowing into the endoscope. Seals 810 and 815 prevent air from the air input from escaping the chamber between seals 810 and 815. It should also be noted that an operator's finger is blocking air flow through the central bore of disposable air/water valve 800. In the depressed position, seal 820 no longer separates the water input and water output. Water from the water input fills the area between seals 815 and 820 and activates the water output to the patient or allows the water to flow out (or be supplied) to the patient. Seal 815 prevents water from escaping up the air/water cylinder of the endoscope.

Although the air/water valve is designed to be used with an endoscope, it will be understood that other medical instruments can be used with the present air/water valve or assembly. These instruments include, for example, colonoscopes, laparo scopes, bronchoscopes, or any medical instruments with a camera that requires air and/or water use.

Figure 9:
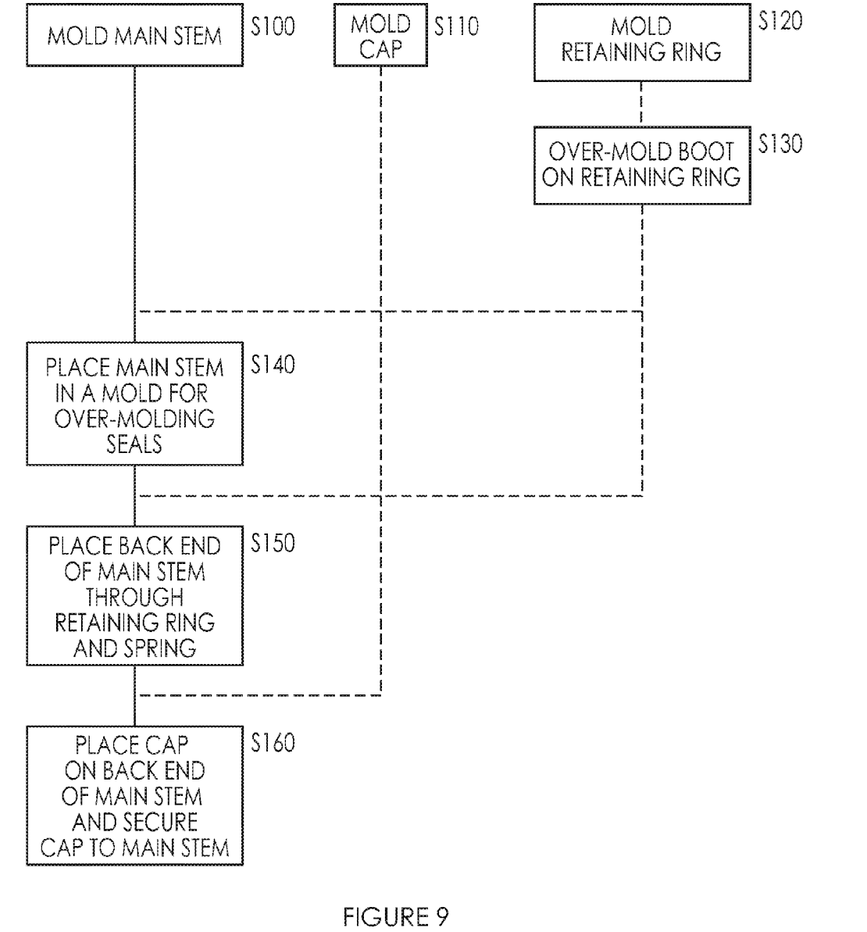
FIG. 9 illustrates an embodiment of a manufacturing process for a disposable air/water valve.

FIG. 9 is a flow chart of a manufacturing process for a disposable air/water valve. The first step S100 of the manufacturing process is molding main stem from a suitable material, such as plastic, polymeric material(s), or any other suitable material(s). Molding the main stem and using lower cost material(s) creates considerable cost savings when compared to the metal used by reusable air/water valves. Additionally, main stem 225 in FIG. 4 is a single piece that does not need to be assembled, like the main stem assembly 100 of a reusable air/water valve, thereby reducing assembly cost. For example, main stem 225 is monolithic (e.g., a single piece) having grooves 227, 222, 221, 219, 217, and ridges 223, 224 and 226 that are molded as part of the main stem. These ridges and/or grooves can be rigid or they can be flexible.

Unlike the non-disposable air/water valves that are not monolithic as many of the ridges and/or grooves are molded separately and contain different material than the main stem, which is metal, the monolithic main stem (one piece) comprises a plurality of ridges and grooves that are the same material as the main stem.

Button cap 245 and retaining ring 230 are also molded in steps S110 and S120. Boot 235 may be over-molded on retaining ring 230 in step S130. Further, in other implementations, boot 235 may be molded separately and simply placed on retaining ring 230 in FIG. 4 during assembly. However, in contrast to main stem 225, button cap 245 and retaining ring 230/boot 235 are not required until later in the manufacturing process. As a result, the dotted lines indicate that steps S110, S120, and S130 may occur at various times in the manufacturing process. Because the boot, button cap, and retaining ring are relatively simple when compared to the main stem, they may be manufactured using additional manufacturing processes that may not be suitable for main stem 225, such as blow molding, over-molding, injection molding, casting, machining, stamping, or any other suitable manufacturing process.

Main stem 225 may be placed in a mold suitable for overmolding seals 205, 210, 215, 220 of FIG. 4 in step S140. For example, the main stem may be placed in a clam-shell like mold and the material utilized to form seals 205, 210, 215, 220 may be injected into the mold. The mold forms the seals 205, 210, 215, 220 of FIG. 4 in seal retaining regions 250, 255, 260, 265. In contrast the seals on reusable air/water valve 10, they slide on the main stem during assembly rather than being over-molded on the main stem, which adds assembly cost.

The seals of the current application can be made from rubber, one or more polymeric material(s), or any other suitable material(s). The seals are preferably made from a pliable material to provide a proper seal when disposable air/water valve 200 is in use. As discussed previously regarding steps S110, S120, and S130, boot, button cap, and retaining ring can be molded at various stages of the manufacturing process. However, note that each of the components must be made before the step they are specifically needed in. For example, retaining ring 230 of FIG. 4 must be molded before step S150 because it is needed in step S150 in the manufacturing process. Similarly, button cap 245 of FIG. 4 is needed before proceeding to step S160 and boot 235 of FIG. 4 is needed before proceeding to step S170.

In step S150, the opening end 270 of FIG. 5 of main stem 225 is placed through the opening in the diaphragm of retaining ring 230 and through resilient member (e.g., spring, rubber, elastic, etc.) 240 of FIG. 4. Button cap 245 may then be placed on the back end 270 of main stem 225 and secured to the main stem 225 in step S160. For example, the disposable air/water valve 200 may be attached (e.g., adhesive, glue, molding, over molding, curing with UV light, welding, ultrasonically welding, or the like or combinations thereof) to secure button cap 245 and the seals 205, 210, 215, 220 to main stem 225. In other implementations, button cap 245 may be secured to main stem 225 using any attachment means (e.g., adhesive, glue, molding, over molding, curing with UV light, welding, ultrasonically welding, mechanical attachment, or the like or combinations thereof) to complete the assembly of disposable air/water valve 200.

It will be recognized by one of ordinary skill in the art that numerous steps in the manufacturing process may be optional or may be performed in a different sequence than specifically shown. The scope of the manufacturing process is not limited to the particular sequence and steps discussed herein, except as expressly recited in the claims.

The air/water valve may be sterilizable. In various embodiments, one or more components of the air/water valve are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

In various embodiments, a kit is provided that may include additional parts along with the air/water valve combined together to be used with the air/water valve. The kit may include the air/water valve device in a first compartment. The second compartment may include a canister holding the air/water valve and any other instruments needed for the procedure. A third compartment may include gloves, drapes, wound dressings and other procedural supplies for maintaining sterility, as well as an instruction booklet. A fourth compartment may include additional cannulas and/or needles. A fifth compartment may include an agent for radiographic imaging. Each device may be separately packaged in a plastic pouch that is radiation sterilized. A cover of the kit may include illustrations of the use of the device and a clear plastic cover may be placed over the compartments to maintain sterility.

Implementations described herein are included to demonstrate particular aspects of the present disclosure. It should be appreciated by those of skill in the art that the implementations described herein merely represent exemplary implementation of the disclosure. Those of ordinary skill in the art should, in light of the present disclosure, appreciate that many changes can be made in the specific implementations described and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

From the foregoing description, one of ordinary skill in the art can easily ascertain the essential characteristics of this disclosure, and without departing from the spirit and scope thereof, can make various changes and modifications to adapt the disclosure to various usages and conditions. The implementations described hereinabove are meant to be illustrative only and should not be taken as limiting of the scope of the disclosure, which is defined in the following claims.

What is claimed is:

1. An air/water valve assembly for an endoscope comprising: a main stem having a proximal end, the main stem being made of a single monolithic thermoplastic piece and comprising a plurality of ridges and grooves disposed circumferentially about the main stem, the plurality of ridges and grooves being monolithic with the main stem and the main stem comprising a first opening disposed at the proximal end and running along a longitudinal axis of the main stem, and a second opening disposed transverse to the first opening, the first and second openings for allowing passage of air and/or fluid through at least a portion of the main stem; and a boot over-molded around surrounding a retainer ring, the retainer ring disposed about the main stem and a resilient member contacting an inner surface of the retainer ring, wherein the retaining ring comprises a diaphragm and an opening having a cutout.

2. An air/water valve assembly according to claim 1, wherein the first and second openings intersect with each other.

3. An air/water valve assembly according to claim 1, wherein a plurality of seals are disposed in the grooves of the main stem.

4. An air/water valve assembly according to claim 3, wherein the plurality of seals comprises four seals disposed in four grooves of the main stem.

5. An air/water valve assembly according to claim 1, wherein the retaining ring, and a button cap are attached to the proximal end of the main stem and a resilient member contacts the retaining ring, and button cap, wherein movement of the resilient member in a downward direction moves the main stem in a downward position.

6. An air/water valve assembly according to claim 5, wherein the button cap comprises a vent running into the first opening of the main stem.

7. An air/water valve assembly according to claim 5, wherein the retaining ring comprises a diaphragm that contacts the resilient member.

8. An air/water valve assembly according to claim 5, wherein the retaining ring is disposed in the center of the main stem, the resilient member comprises a spring that contacts the retaining ring and the button cap and the button cap is disposed at the proximal end of the main stem.

9. An air/water valve assembly according to claim 1, wherein the main stem comprises a distal end and the distal end is solid.

10. An air/water valve assembly according to claim 1, wherein the air/water valve assembly is used in an endoscopic procedure.

11. An air/water valve assembly according to claim 1, wherein the opening cutouts are semi-circular.

12. An air/water valve assembly according to claim 1, wherein at least one seal is over-molded onto the main stem; and at least one seal is over-molded to at least one groove or ridge.

13. An air/water valve assembly according to claim 1, wherein the stem and grooves and ridges are made from the same thermoplastic material.

14. An air/water valve assembly according to claim 1, wherein the main stem comprises at least two ridges, each of the at least two ridges having a diameter, wherein one of the at least two ridges has a larger diameter than the other ridge.

15. An air/water valve assembly according to claim 1, wherein the main stem comprises at least two grooves, each of the at least two grooves having a diameter, wherein one of the at least two grooves has a larger diameter than the other groove.

16. An air/water valve assembly for an endoscope comprising: a main stem having a proximal end, the main stem being made of a single monolithic thermoplastic piece and comprising a plurality of ridges and grooves disposed circumferentially about the main stem, the plurality of ridges and grooves being monolithic with the main stem and the main stem comprising a first opening disposed at the proximal end and running along a longitudinal axis of the main stem, and a second opening disposed transverse to the first opening, the first and second openings intersecting with each other and configured to allow passage of air and/or fluid through at least a portion of the main stem; a plurality of seals disposed in the plurality of grooves disposed circumferentially about the main stem; a retainer ring contacting and disposed around the main stem, wherein the retaining ring comprises a diaphragm and an opening having a cutout; a button head or button cap contacting the proximal end of the main stem; a resilient member contacting an inner surface of the retainer ring and the button head or button cap; and a boot over-molded around surrounding the retainer ring, wherein application of a downward force to the button head or button cap causes the main stem to move in a downward position.

17. An air/water valve assembly according to claim 16, wherein the main stem comprises a distal end and the distal end is solid.

18. An air/water valve assembly according to claim 16, wherein the button cap comprises a vent running into the first opening of the main stem.

19. An air/water valve assembly according to claim 1, wherein the diaphragm that contacts the resilient member.

20. An air/water valve assembly according to claim 16, wherein at least one seal is over-molded onto the main stem; and at least one seal is over-molded to at least one groove or ridge.

21. An air/water valve assembly according to claim 16, wherein the main stem comprises at least two ridges, each of the at least two ridges having a diameter, wherein one of the at least two ridges has a larger diameter than the other ridge.

22. An air/water valve assembly according to claim 16, wherein the main stem comprises at least two grooves, each of the at least two grooves having a diameter, wherein one of the at least two grooves has a larger diameter than the other groove.

23. An air/water valve assembly for an endoscope comprising: a main stem having a proximal end, the main stem being made of a single monolithic thermoplastic piece and comprising a plurality of ridges and grooves disposed circumferentially about the main stem, the plurality of ridges and grooves being monolithic with the main stem and the main stem comprising a first opening disposed at the proximal end and running along a longitudinal axis of the main stem, and a second opening disposed transverse to the first opening, the first and second openings for allowing passage of air and/or fluid through at least a portion of the main stem; and a boot surrounding a retainer ring, wherein the retaining ring comprises a diaphragm and an opening having a cutout; the retainer ring disposed about the main stem and a resilient member contacting an inner surface of the retainer ring; wherein the main stem comprises at least two ridges, each of the at least two ridges having a diameter, wherein one of the at least two ridges has a larger diameter than the other ridge.

* * * * *